US006547783B1

(12) United States Patent
Vilendrer et al.

(10) Patent No.: US 6,547,783 B1
(45) Date of Patent: Apr. 15, 2003

(54) THERMO-ELECTRIC GRIP FOR HOLDING SOFT TISSUE

(75) Inventors: Kent Vilendrer, Eden Prairie, MN (US); Kelly Grimes, Minneapolis, MN (US); Jagdeesh Shukla, Minneapolis, MN (US); David Strei, Chaska, MN (US); Christopher Eriksen, St. Paul, MN (US); Troy Nickel, St. Louis Park, MN (US)

(73) Assignee: EnduraTEC Systems Corp., Minnetonka, MN (US)

( * ) Notice: Subject to any disclaimer, the term of this patent is extended or adjusted under 35 U.S.C. 154(b) by 16 days.

(21) Appl. No.: 09/695,497

(22) Filed: Oct. 24, 2000

(51) Int. Cl.$^7$ ............................................... A61B 18/62
(52) U.S. Cl. ............................. 606/20; 607/96; 607/99
(58) Field of Search ................................ 606/20; 62/293

(56) References Cited

U.S. PATENT DOCUMENTS

| | | | |
|---|---|---|---|
| 3,369,550 A | * | 2/1968 | Armao .................. 606/20 |
| 3,766,910 A | | 10/1973 | Lake .................... 128/20 |
| 4,440,167 A | * | 4/1984 | Takehisa ............... 606/20 |
| 4,860,744 A | | 8/1989 | Johnson et al. ........ 128/303.1 |
| 5,207,674 A | | 5/1993 | Hamilton .............. 606/20 |
| 5,300,065 A | | 4/1994 | Anderson ............... 606/13 |
| 5,458,596 A | | 10/1995 | Lax et al. ............. 606/31 |
| 5,569,242 A | | 10/1996 | Lax et al. ............. 606/42 |
| 5,674,218 A | | 10/1997 | Rubinsky et al. ....... 606/20 |
| 5,755,660 A | | 5/1998 | Tyagi .................. 600/205 |
| 5,776,130 A | | 7/1998 | Buysse et al. ......... 606/48 |
| 5,873,254 A | | 2/1999 | Arav ................... 62/63 |
| 5,891,142 A | | 4/1999 | Eggers et al. ......... 606/51 |
| 6,042,539 A | | 3/2000 | Harper et al. ......... 600/201 |
| 6,059,783 A | | 5/2000 | Kirwan, Jr. ........... 606/51 |
| 6,074,389 A | | 6/2000 | Levine et al. ......... 606/45 |
| 6,091,995 A | | 7/2000 | Ingle et al. .......... 607/138 |
| 6,096,032 A | | 8/2000 | Rowland ............... 606/20 |
| 6,113,559 A | | 9/2000 | Klopotek .............. 601/3 |
| 6,350,262 B1 | * | 2/2002 | Ashley ................ 606/32 |

* cited by examiner

*Primary Examiner*—Roy D. Gibson
*Assistant Examiner*—Henry M. Johnson, III
(74) *Attorney, Agent, or Firm*—C. G. Mersereau, Esq.; Nikolai & Mersereau, P.A.

(57) ABSTRACT

A grip for holding soft materials is described wherein the gripping surface of the grip is cooled by a thermo-electric cooler. The grip of the present invention includes grip members having opposed gripping surfaces that contact the soft material. The grip does not require use of cryogenic materials and is suitable for use in contact with fluids at body temperature. The temperature of the grip can be easily controlled.

24 Claims, 9 Drawing Sheets

THERMO-ELECTRIC GRIP FOR HOLDING SOFT TISSUE

FIELD OF THE INVENTION

This invention relates generally to a device for holding soft, pliable objects or materials, and more particularly relates to a medical device for holding soft tissue. The present invention includes a grip having opposed gripping surfaces that contact the soft tissue. The gripping surfaces are cooled to thereby freeze the tissue adjacent the gripping surface. In this manner, the grip may be clamped onto the frozen tissue with an applied load sufficient to hold the tissue within the grip. The frozen tissue withstands the compression forces of the grip without greatly deforming the soft tissue. All the tissue adjacent the gripping surface freezes, thereby distributing the clamping load of the grip equally among the fibers and further reducing potential tissue damage.

BACKGROUND OF THE INVENTION

In the past, medical devices have been utilized to attempt to hold in place soft pliable tissue. These devices typically include a grip member that clamps, pinches, grasps or otherwise attempts to hold the soft tissue. The grip member of these devices typically only holds in place the outside surface of the soft tissue. Because biological tissue is soft, the central portion of the test sample is not held stationary by the grip member. Further, biological tissue such as skin, muscle, and tendon is commonly very slippery and slips out of the grip members. Also, soft tissue has a very low coefficient of friction, and compression of the tissue causes expression of fluid, which creates a slippery film and further decreases the coefficient of friction for the tissue. Hence, the tissue must be gripped with enough force to avoid slipping between the grip members when a load or force is applied to the tissue in a direction away from the gripping members.

The large compressive forces that are required to grip the tissue without slipping may cause large deformations of the tissue and often results in failure of the tissue at the grip interface. Further, clamping or tightening the grip members may cause damage to the tissue. Grip members with roughened surfaces that rely on large compression forces often sever or otherwise damage some of the fibers in the tissue. Attachment of the tissue to the gripping members with the use of sutures instead of compression devices almost always causes failure of the tissue at the suture site.

Various medical devices have been utilized to test the mechanical properties of a test sample of tissue. This material testing equipment may, for example, typically requires holding the test sample at opposite ends and repeatedly stretching the tissue. Any slipping of the tissue test sample within the grips during testing will affect the accuracy of the test results. Further, if the sample partially fails or is damaged, the accuracy of the results is affected. Also, large deformations of the clamped part of the tissue also cause unequal load distribution among the fibers, leading to unreliable test results.

In an attempt to increase the accuracy of the material testing equipment, the ends of the test sample may be frozen. By freezing the sample when it is lightly clamped between the gripping members and conforming to the surface of the grip, the sample becomes mechanically rigid and stiff enough to prevent the sample from being damaged and also from slipping out of the grip. Since the sample is not frozen over its entire length, freezing the ends of the sample do not typically affect the results of mechanical tests of the test specimen.

In the past, the ends of the test sample have been frozen using a cryogenic material such as liquid carbon dioxide, dry ice or liquid nitrogen. The cryogenic material may be applied to freeze the grip and test sample by, for example, circulating the cryogenic liquid through passages formed in the grip. Typically, only one half of the grip is cooled, requiring adequate insulation of the other side of the grip to avoid at least partial thawing of the test sample. Also, use of cryogenic liquids requires special handling and storage procedures and the cryogenic liquid must be applied continuously to avoid thawing of the sample.

Further, grips cooled with cryogenic liquids are not compatible with environmental chambers used during the testing of biological materials. For example, many biological materials must be tested under biological conditions (37° C. and wet) to obtain accurate test results of the sample tissue. Typically, the entire sample and grip are submersed in a saline bath that is maintained at 37° C. Grips that use cryogenic liquids to freeze the test sample also freeze the water in the saline bath, or at least make it difficult to maintain the bath at the desired temperature. Additionally, temperature control of these grips requires special valves designed for cryogenic materials. Hence, a need exists for a gripping member that holds the biological tissue and reduces the potential that the test sample will slip within the grip without the use of cryogenic liquids. The present invention meets these and other needs that will become apparent from a review of the description of the present invention.

SUMMARY OF THE INVENTION

The present invention is directed to a thermoelectric grip for gripping soft materials including, without limitation tissue, wherein the grip freezes the portion of the tissue that contacts the grip without the use of cryogenic liquids. The thermoelectric grip of the present invention generally includes first and second spaced apart opposing grip members. Each grip member has an outer gripping surface and a thermoelectric cooler adapted for cooling the outer gripping surface. The thermoelectric cooler is isolated electrically from the outer gripping surface. The grip members of the present invention may include actuating members coupled thereto, wherein the actuating members actuate the first and second grips to change a separation distance between the first and second grip members.

In use, the grip members freeze the soft tissue that contacts the outer gripping surface. The entire end of the tissue in contact with the gripping surface may freeze, rather than just an outer portion of the soft tissue. A controller may be electrically coupled to the thermo-electric cooler to control a temperature at the outer gripping surface and the controller may also control a rate of cooling the outer gripping surface. In the preferred embodiment, the outer gripping surface includes a removable jaw plate, wherein the jaw plate includes an outer contoured surface suitable for gripping various sized soft tissue. Those skilled in the art will appreciate that, without limitation, the grip of the present invention may form a gripping end of a forceps, the gripping end of a surgical instrument, or the grip of material testing equipment, to name just a few devices used to grip soft tissue.

The grip of the present invention allows the holding and/or testing of biological tissue without damaging the tissue and without breaking the tissue at the grip site, while also preventing slippage of the tissue out of the grip. The grip also enables accurate testing of biological and soft materials, to accurately determine the properties of the tissue sample. The thermoelectric grip of the present invention may be sized appropriately to work with a wide range of tissue sizes. By making the jaw face of the grip easily replaceable, each grip may be used for many different sample shapes and many different test types.

Those skilled in the art will appreciate that a thermoelectrically cooled grip offers several advantages over cryogenic liquid cooled grips. For example, without limitation, thermoelectric coolers use electricity to generate freezing temperatures, thereby eliminating the need to purchase, handle, and store cryogenic materials. Also, the temperature of the thermoelectric cooler is readily controlled and the zone of cooling may also be controlled. In this manner, the thermo-electric grip of the present invention is suitable for use in a liquid bath without freezing the liquid around the grip. Further, standard temperature controllers may be used to control the temperature of the grip and thus the amount of the tissue that is frozen.

These and other advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION

The present invention represents broadly applicable improvements to grips for holding soft materials including soft tissue. The embodiments detailed herein are intended to be taken as representative or exemplary of those in which the improvements of the invention may be incorporated and are not intended to be limiting. For purposes of discussion, and without any limitation intended, the grip 10 of the present invention will be described in conjunction with a medical instrument, a material testing system, and an electro-surgical forceps. Those skilled in the art will appreciate that a variety of other devices that utilize grips to hold soft pliable materials or objects may utilize the grips of the present invention.

The grip of the present invention does not require a cryogenic material, may be controlled and monitored using an electronic temperature controller, and is operable in an environmental chamber and saline bath.

Generally, the grip of the present invention includes two spaced apart gripping members, a temperature controller, and a cooling system that cools an outer surface of the gripping members. The temperature controller is used to control the temperature of the outer surface of the gripping members and the cooling system is used to cool the gripping members. In the preferred embodiment, a thermoelectric cooler is used to cool the outer surface of the gripping members. To control the temperature of the outer surface of the gripping members, temperature controllers of known suitable construction may be used to monitor the temperature of the gripping members and control the voltage to the thermoelectric coolers. Additionally, the rate of cooling the gripping members may be controlled by a suitable temperature controller of known suitable construction, to thereby minimize damage to the biological sample caused by freezing it too fast.

Without limitation, in the preferred embodiment an RTD (resistance temperature detector) is placed between the outer surface of the gripping member and the thermoelectric cooler. The RTD provides the input temperature for the temperature controlling system. An additional RTD is placed between the thermoelectric cooler and a cooling plate to measure the temperature at the hot side of the thermoelectric cooler. The information obtained from the RTD may be used by the temperature controlling system to shut off power to the thermoelectric cooler if the thermoelectric coolers overheat. The temperature controller system will also shut off power to the system if the thermo-electric coolers shut down.

The thermoelectric cooler only generates freezing temperatures on one side, the side adjacent the outer surface of the gripping members, wherein the grip only freezes the tissue placed between and in contact with the gripping members. Thus, when the grip is utilized in environmental chambers and saline baths, the temperature of the surrounding saline or media remains relatively unchanged by the cooling of the gripping surface of the gripping members.

In an alternate embodiment of the present invention, the RTDs may be interfaced with a computer processing unit that controls the power and temperature of the thermoelectric coolers. Alternatively, the thermo-electric coolers may operate continuous at full power, eliminating the need for temperature controllers. An AC to DC converter would still be needed to power the grips. Also, rather than cooling the hot side of the thermo-electric cooler with a flow through cooling system. a heat sink could replace the cold plate on the hot side of the thermo-electric cooler. In this embodiment, a fan may be utilized to keep a constant air flowing past the heat sinks to enhance cooling of the hot side of the thermoelectric cooler.

Figure 1:
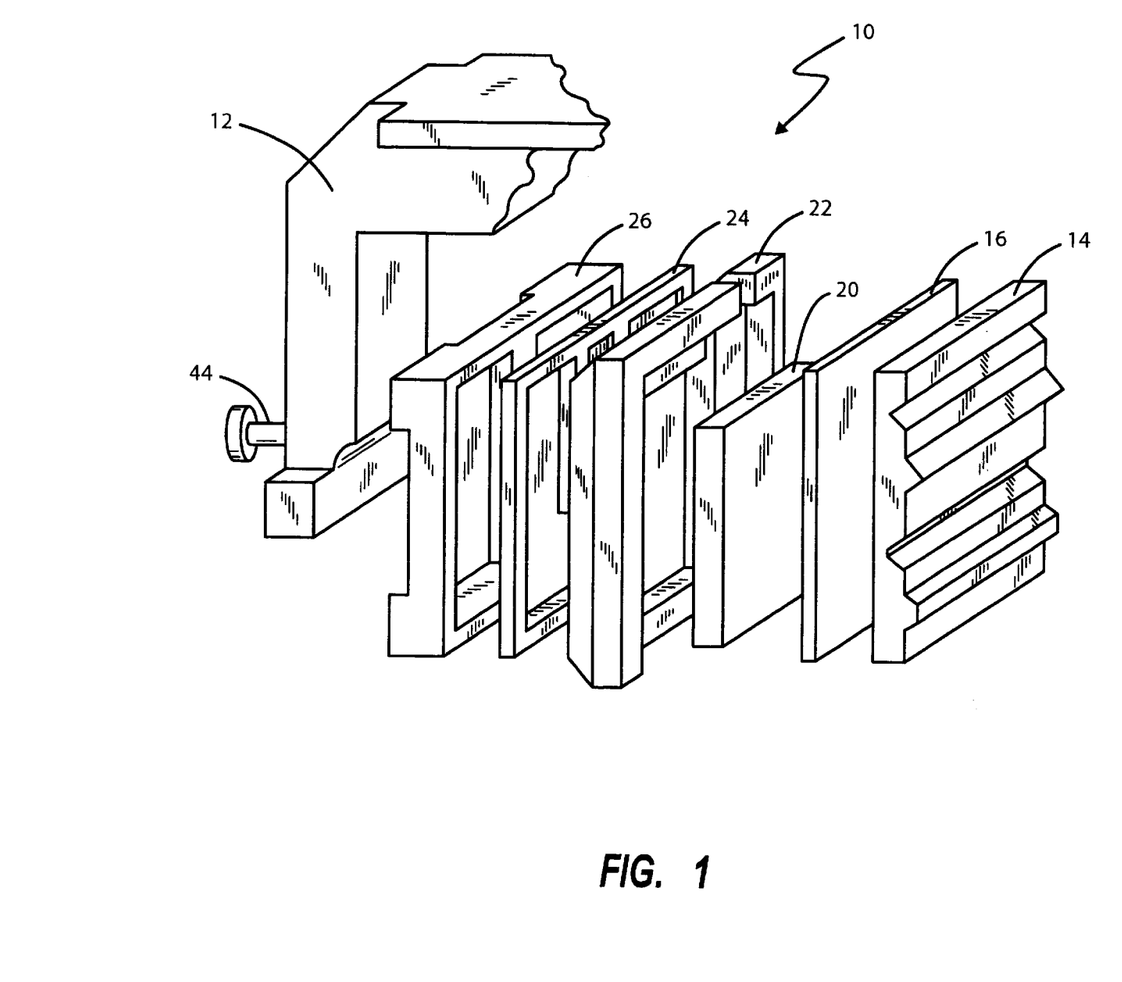
FIG. 1 is a partial fragmented exploded perspective view of a thermo-electric grip of the present invention.

Having described details of the invention, further details with specific reference to the Figures will next be presented. The several Figures illustrate several embodiments of the invention wherein the thermo-electric grip may be used for gripping soft tissue. With reference first to FIG. 1 the grip system 10 of the present invention is shown mounted to a support 12 of a material testing system. Without any limitation intended, the grip system 10 of the preferred embodiment generally includes opposed gripping devices 11. Each gripping device 11 includes a removable jaw plate 14, jaw sub-plate 16, temperature sensor 18 (see FIG. 5), thermo-electric cooler 20, spacer 22, sealing plate 24, cooling plate 26, and temperature sensor 28 (see FIG. 5).

Figure 5:
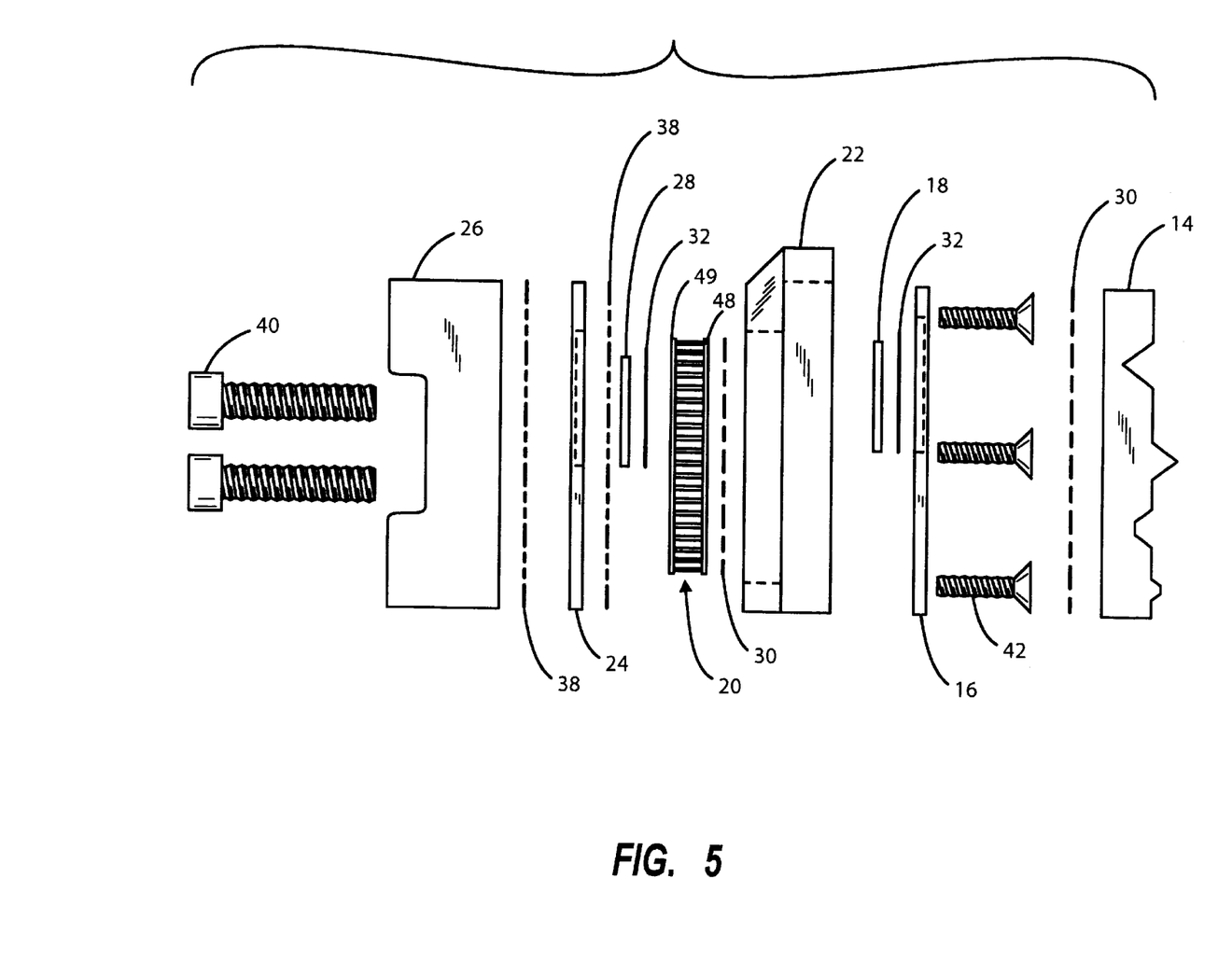
FIG. 5 is an exploded side elevational view of the thermo-electric grip of the type shown in FIG. 1.

FIG. 5 shows further detail of the gripping devices 11. A thermal grease 30 of known suitable construction is positioned between the removable jaw plate 14 and jaw sub-plate 16. An epoxy 32 of known suitable construction is used to hold the temperature sensor (RTD) 18 in a groove formed in the jaw sub-plate 16. The spacer 22 includes a cavity in which the thermo-electric cooler 20 fits and thermal grease 30 is positioned between the thermal electric cooler 20 and the jaw sub-plate 16. Epoxy 32 is used to hold the temperature sensor (RTD) 28 against the thermo-electric cooler 20. Sealant 38 seals the cooling plate 26 to the sealing plate 24 and the sealing plate 24 to the spacer 22. Screws 40 extend through the cooling plate 26, sealing plate 24, spacer 22, jaw sub-plate 16, and hold the removable jaw plate 14 against the jaw sub-plate 16. Screws 42 fasten together the cooling plate 26, sealing plate 24, spacer 22, and jaw sub-plate 16, thereby engaging the thermo-electric cooler against the sealing plate 24 and jaw sub-plate 16.

Figure 2:
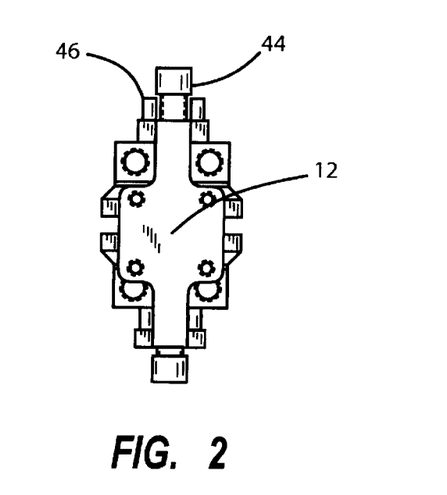
FIG. 2 is a top plan view of the thermo-electric grip of the type shown in FIG. 1.
Figure 3:
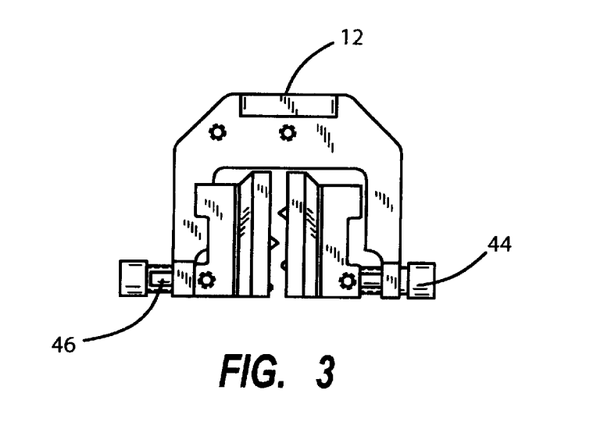
FIG. 3 is a front elevational view of the thermo-electric grip of the type shown in FIG. 1.
Figure 4:
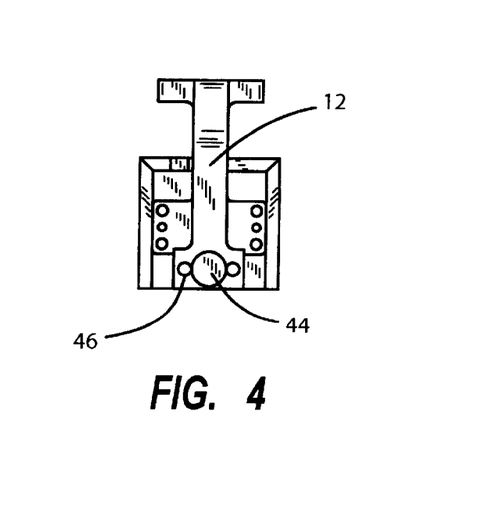
FIG. 4 is a side elevational view of the thermo-electric grip of the type shown in FIG. 1.

FIGS. 2–4 shows the assembled grip 10 mounted to support member 12. An actuating member 44, typically a rotatable screw device, and alignment pins 46 extend through the support member 12 and the actuating member is attached to gripping devices 11. Rotation of the actuating member 44 moves the grip member relative to the support member 12, allowing the user to change the separation distance between the gripping devices 11 and, consequently, the gripping force on a captured object.

Figure 6:
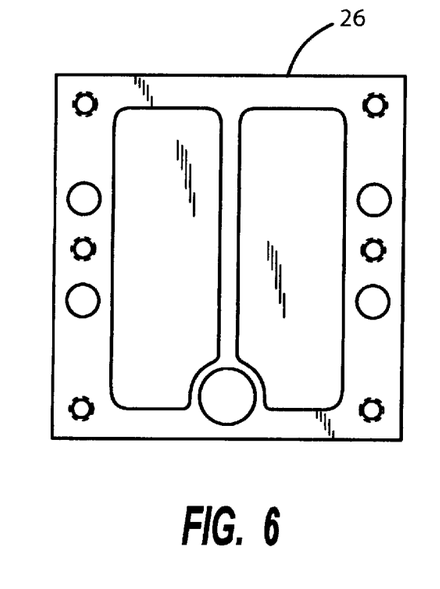
FIG. 6 is a front elevational view of a cooling plate of the thermo-electric grip of the type shown in FIG. 1.
Figure 7:
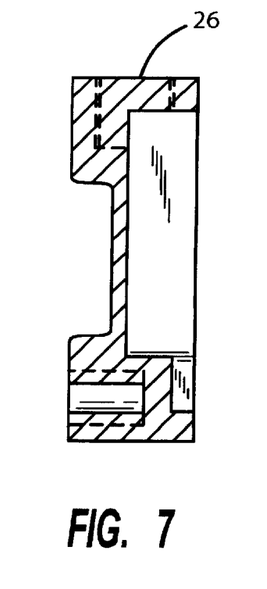
FIG. 7 is a partial sectional side elevational view of the cooling plate of the type shown in FIG. 6.
Figure 8:
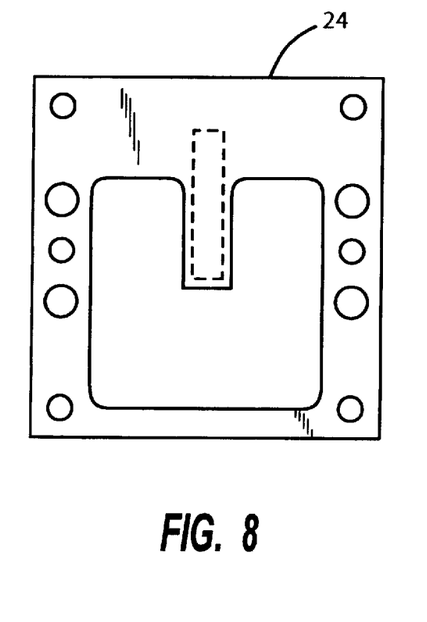
FIG. 8 is a front elevational view of a sealing plate of the thermo-electric grip of the type shown in FIG. 1.
Figure 9:
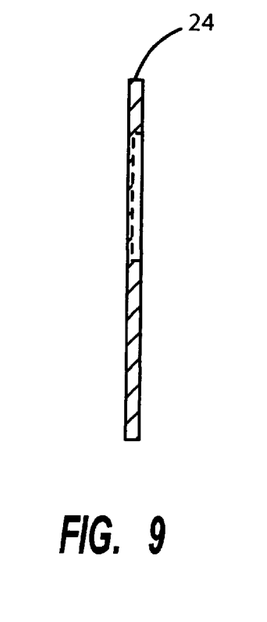
FIG. 9 is a partial sectional side elevational view of the scaling plate of the type shown in FIG. 8.
Figure 10:
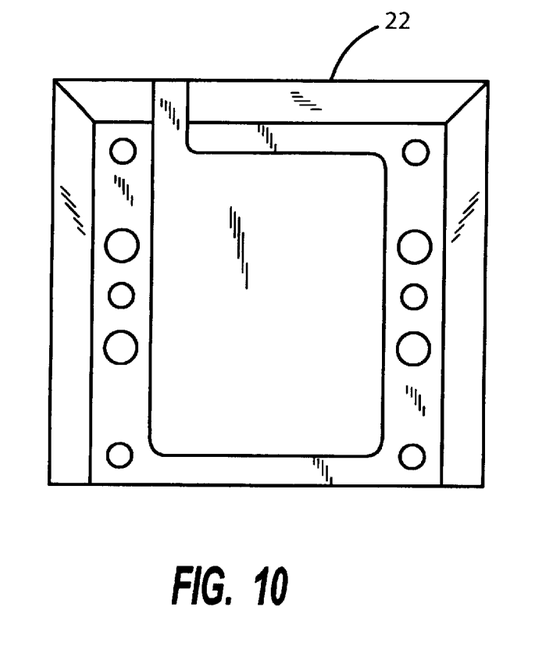
FIG. 10 is a front elevational view of a spacer plate of the thermoelectric grip of the type shown in FIG. 1.
Figure 11:
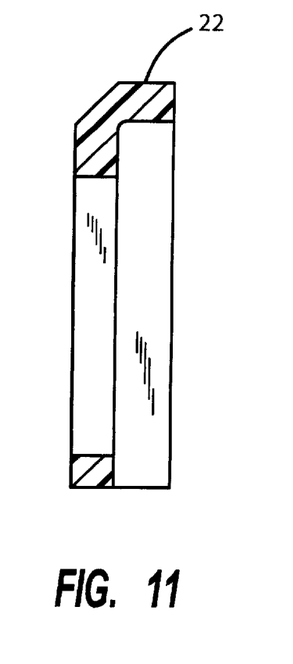
FIG. 11 is a partial sectional side elevational view of the spacer plate of the type shown in FIG. 10.
Figure 12:
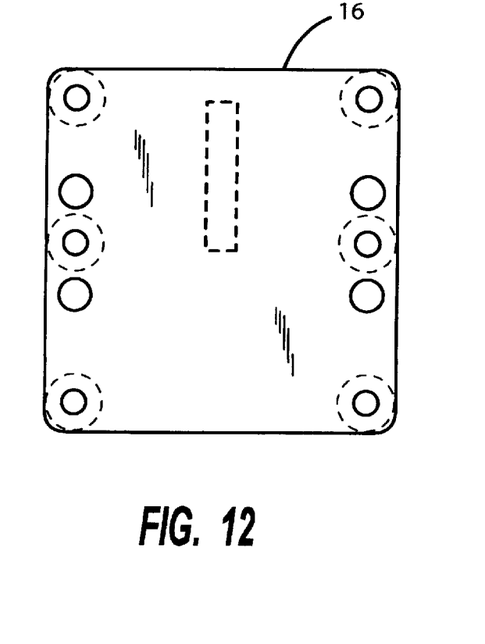
FIG. 12 is a front elevational view of a spacer sub plate of the thermoelectric grip of the type shown in FIG. 1.
Figure 13:
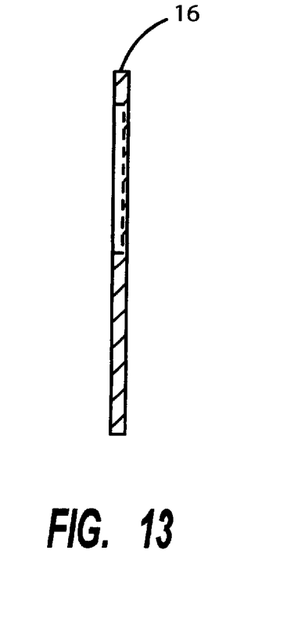
FIG. 13 is a partial sectional side elevational view of the spacer sub plate of the type shown in FIG. 12.

FIGS. 6–13 shows additional details of the jaw sub-plate 16 (see FIGS. 12–13), spacer 22 (see FIGS. 10–11), sealing plate 24 (see FIGS. 8–9), and cooling plate 26 (see FIGS. 6–7). Without any limitation intended, the thermo-electric cooler 20 is of the type having a cooling plate 48 aligned adjacent the jaw sub-plate 16 and a hot plate 49 aligned adjacent the sealing plate 24 and cooling plate 26. In this manner, cooling liquid from a cooling system may be circulated past the hot side 49 of the thermo-electric cooler 20 while containing the cooling liquid within the grip system 10. The jaw plate 14, jaw sub-plate 16, sealing plate 24 and cooling plate 26, without limitation, are preferably made from titanium. The cooling system may consist of a water pump, a water to air heat exchanger, a fan, and a water reservoir (not shown). The cooling system preferably removes a total of 180 watts of heat from the water (90 watts for each grip). It has been determined that for a 1.5 inch square jaw plate, 30 watts of heat needs to be removed from the jaw plate in contact with tissue at 98° F. to maintain the jaw plate 14 at 20° F. To provide 30 watts of cooling power, the thermo-electric coolers typically require about 60 watts of electrical power.

The embodiment shown in FIGS. 1–13 illustrates a grip 10 having a liquid cooled thermo-electric cooler 20. Those skilled in the art will appreciate that other known suitable devices may be used to cool the hot side 49 of the thermo-electric cooler 20. For example, a heat sink could be used to cool the thermoelectric cooler 20 using either natural convection, without a fan, or with forced convection, where a fan is used to force air over the heat sink. The heat sink could be designed to operate in environmental chamber.

Figure 14:
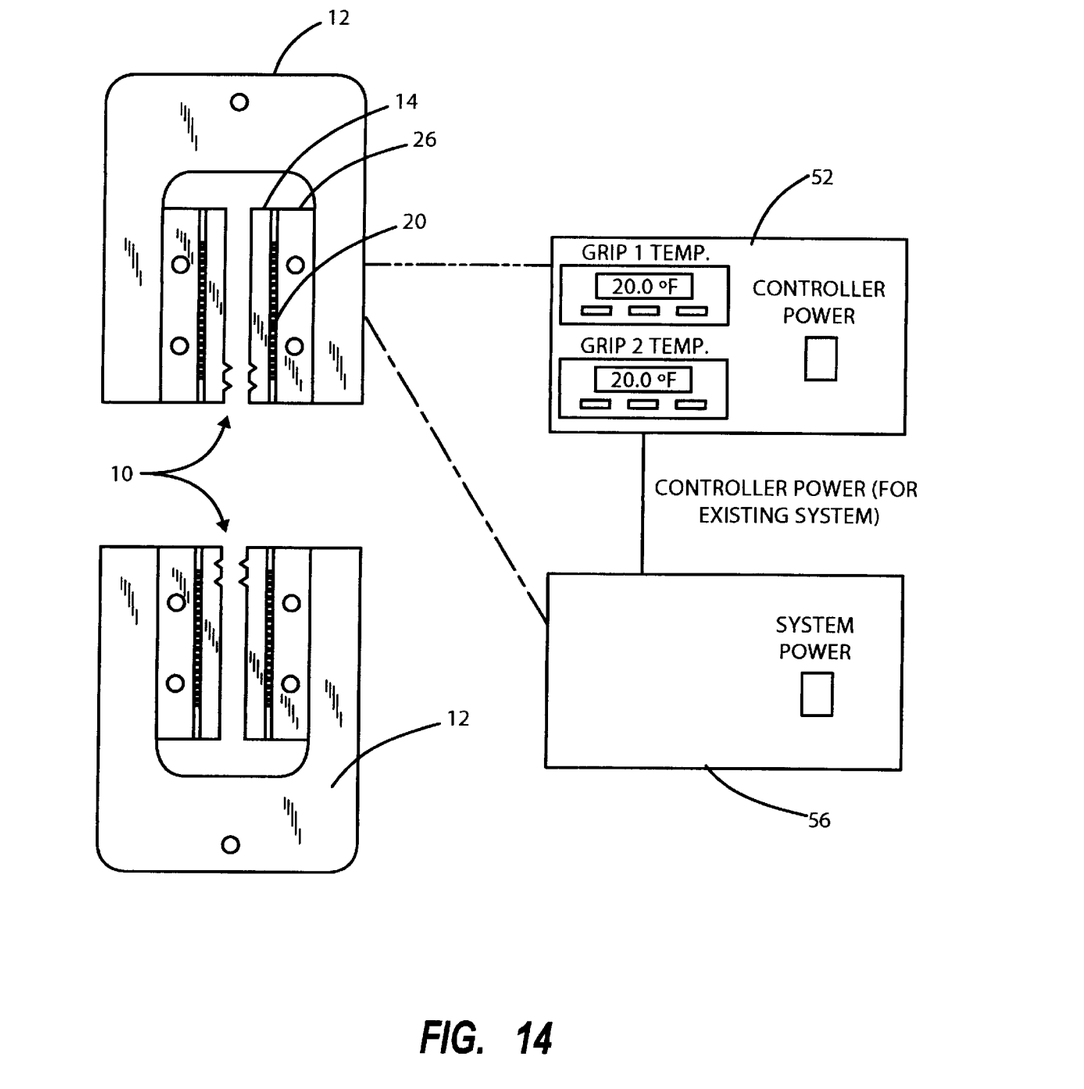
FIG. 14 is a partial sectional front elevational view of an alternate embodiment of the thermo-electric grip of the present invention shown coupled to a controller of the thermoelectric cooler.
Figure 15:
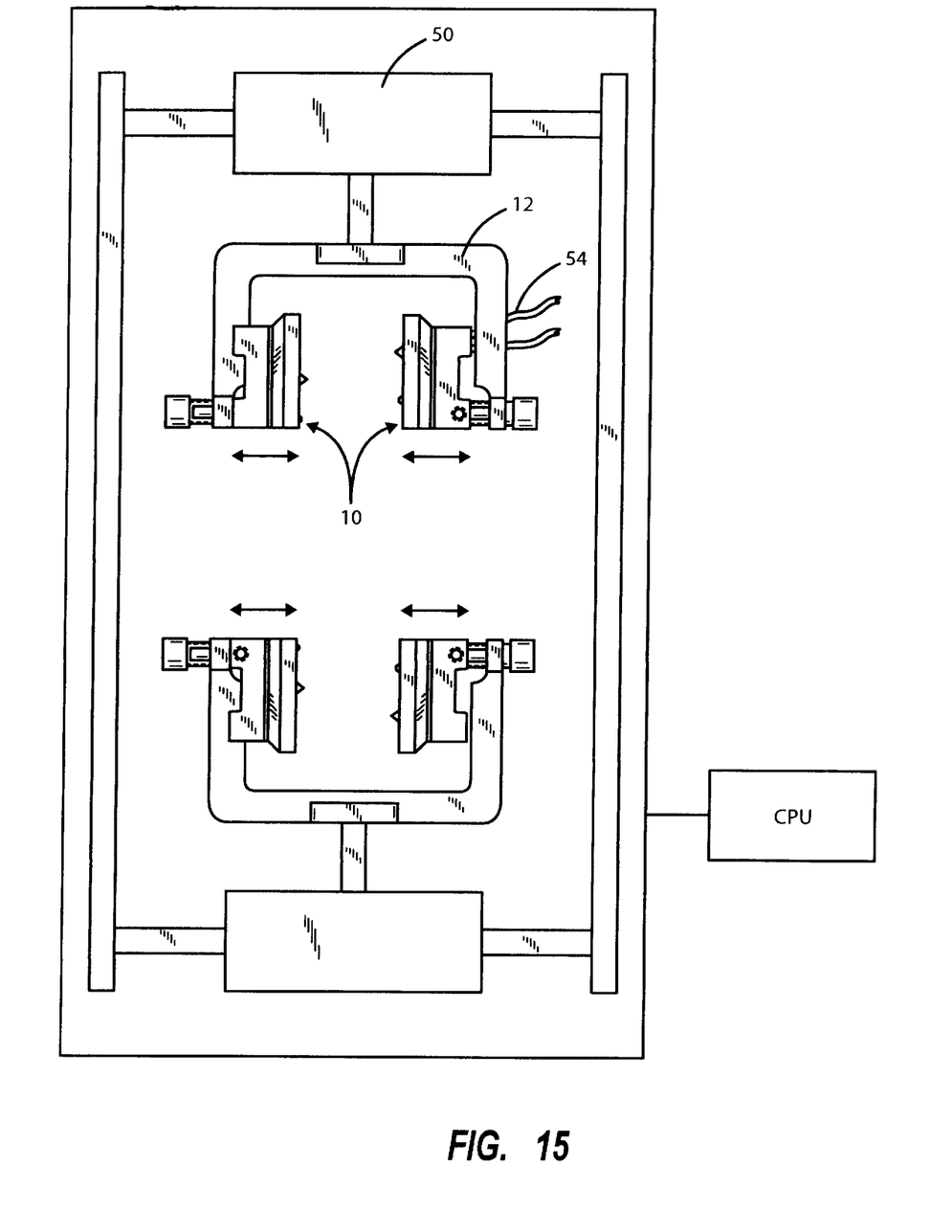
FIG. 15 is a side elevational view showing a thermoelectric grip of the present invention used to hold tissue in a material testing system.

Referring now to FIGS. 14 and 15, the grip system 10 is shown mounted to the support member 12 of a material testing system 50. FIG. 14 shows the grip 10 electrically coupled to a temperature control system 52 and power supply 56. Alternatively, FIG. 15 shows the grip 10 electrically coupled to a Computer Processing Unit (CPU) 58 capable of controlling the temperature of the jaw sub-plate 16, the temperature of the liquid coolant, and the rate of cooling the jaw sub-plate 16. Conduits 54 provide a passage for the liquid coolant to the gripping devices 11.

Figure 16:
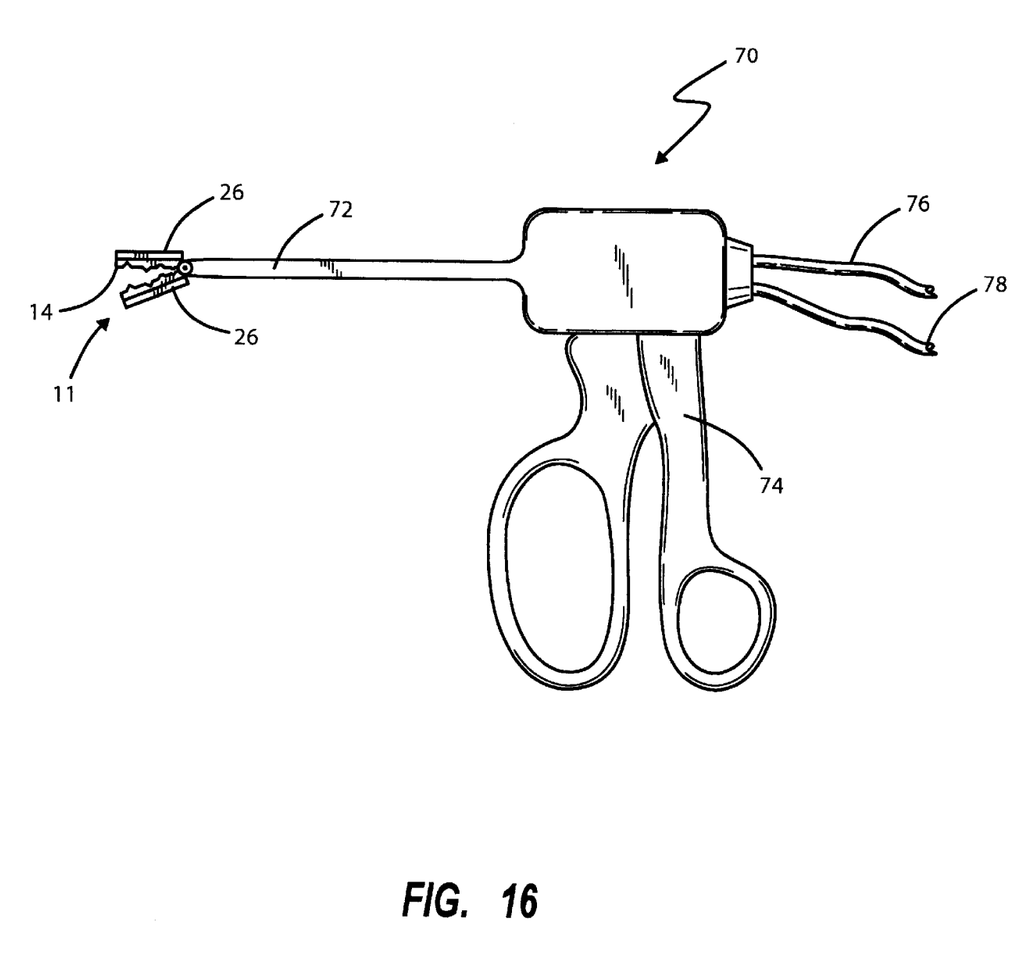
FIG. 16 is a side elevational view showing a thermoelectric grip of the present invention forming a gripping end of a medical instrument.

FIG. 16 shows a medical instrument of known suitable construction in the form of a hand-held scissor arrangement having opposing gripping devices 11 pivotally attached to the end of an elongated rod 72 of a medical instrument 70. The medical instrument includes an internal mechanism (not shown) of known suitable construction linked to the handle 74 and each gripping devices 11 to actuate the grip members open and closed. Electrical lead 76 is electrically coupled to the thermo-electric cooler contained within each gripping device 11. A coolant supply line 78 may extend through the elongated rod 72 to the distal end to allow saline to be directed past the cooling plates 26 thereby cooling the hot side of the thermo-electric cooler. Alternatively, the cooling plates may be air cooled.

Figure 17:
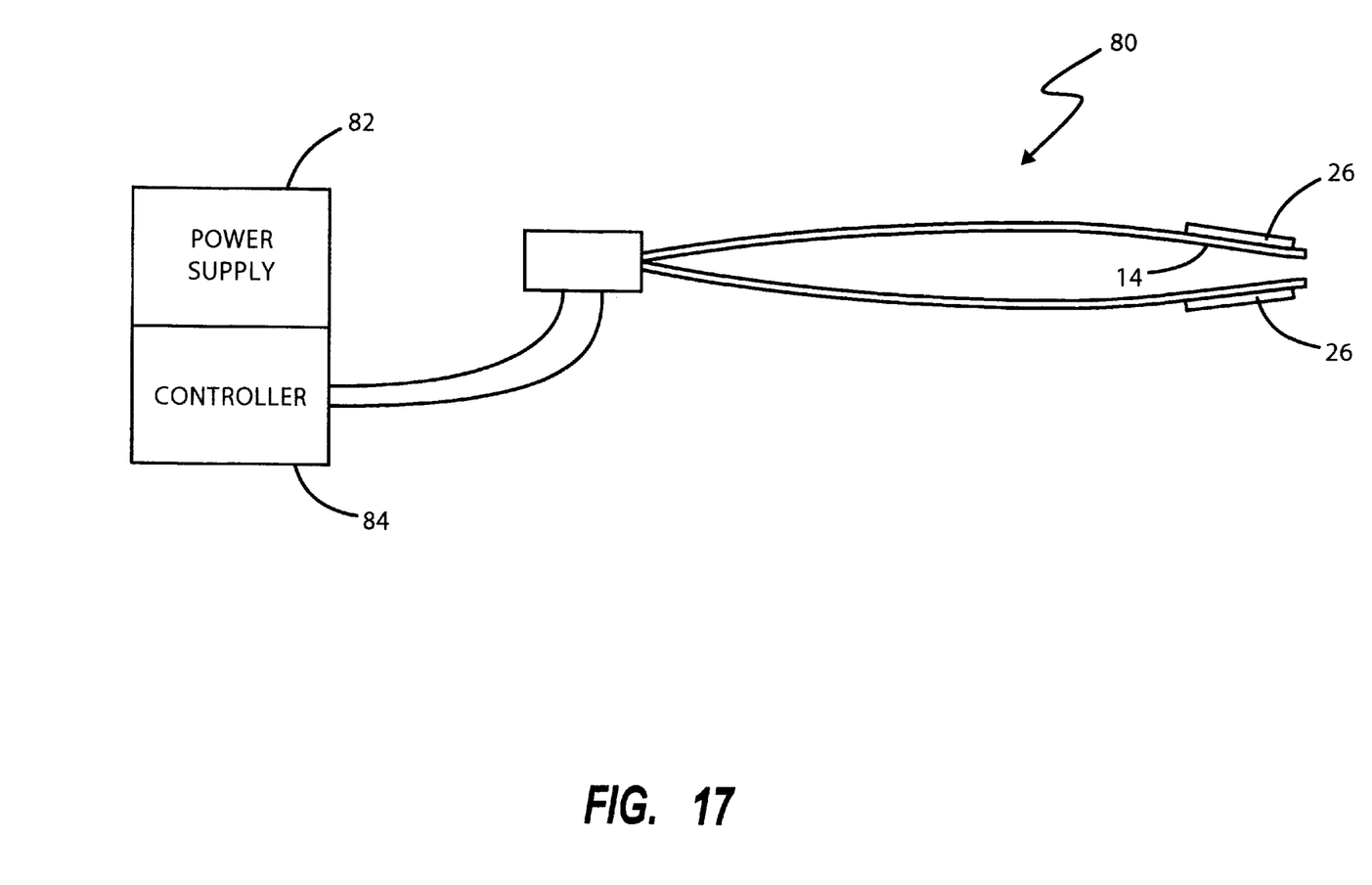
FIG. 17 is a side elevational view showing a thermoelectric grip of the present invention forming a gripping end of an electro-surgical forceps.

FIG. 17 shows yet another embodiment of the grip system 10 that takes the form of medical forceps 80 having a pair of opposed tension members 86 and 88. The forceps are electrically coupled to a power supply 82 and controller 84. The distal end of the forceps includes spaced apart gripping devices 11, wherein the gripping surface of each gripping device is cooled by a thermo-electric cooler 20 contained within each gripping device 11.

Having described the constructional details of the present invention, the mode of use will next be presented. Those skilled in the art will appreciate that the grip system 10, may be utilized to grip tissue in many of several applications including a material testing system, medical forceps or other medical instrument. First, the user actuates the opposing gripping devices 11 together until the grip members contact the tissue. Electrical power is then supplied to the thermo-electric coolers 20. The temperature control system may be utilized to control the amount of power supplied to the thermal-electric coolers 20. When power is supplied to the thermoelectric coolers 20 by the temperature control system, the front side or cool side 48 (the side closest to the jaw sub-plate 16) will fall in temperature and the back side or hot side 49 of the thermo-electric cooler 20 will rise in temperature. Because the front side of the thermo-electric cooler is falling in temperature, heat will be conducted through the thermally conductive grease 30 and jaw sub-plate 16 causing the removable jaw plate 14 to also fall in temperature. When the temperature of the jaw plate 14 falls below 32° F. the test sample freezes.

All of the heat entering the thermo-electric cooler 20 on the cold side 48 must be dissipated as heat on the hot side 49. To dissipate this heat, cooling plate 26 has liquid passages that allow a coolant to be circulated through them. The coolant enters the cooling plate 26, heats up as it passes over the thermo-electric cooler 20, and then exits the cold plate 26 to return to the cooling system (described above but not shown).

To control the temperature of the grip system 10, temperature sensors 18 and 28 sense the temperature of the jaw sub-plate 16 and hot side 49 of the thermo-electric cooler. Signals corresponding to the temperatures sensed by the sensors 18 and 28 are relayed to a CPU or temperature control system 52. The temperature control system 52 can independently control the temperature of each gripping device 11. Based on the temperature reading of the jaw sub-plate 16, the temperature control system will adjust the power input to the thermo-electric cooler 20 to maintain the jaw sub-plate 16 at a desired temperature.

In addition to freezing the test sample, the jaw plate 14 is configured to enhance the grip on the test sample. The configuration on the outer surface of each jaw plate 14 may include a series of ridges that will interlock with valleys on the opposite jaw plate. The jaw plates 14 are removable and the user may substitute one jaw plate having a predefined outer surface configuration with another jaw plate having a different configuration that may enhance the gripping of the soft tissue. When it is desired to test a test sample in an environmental chamber or in a fluid chamber, the test sample is first loaded into the grip system 10 as previously described. Test fluid is then pumped into the environmental chamber at an elevated temperature to simulate body fluid temperatures. The test fluid is maintained at the elevated temperature by a heater. The grips 10 of the present invention have little affect on the temperature of the test fluid.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices and that various modifications, both as to the equipment and operating procedures, can be accomplished without departing from the scope of the invention itself. For example, without limitation, different methods of cooling the hot side of the thermo-electric cooler 20, and different temperature control systems may be utilized without departing from the intended scope of the present invention.

What is claimed is:

1. A thermo-electric grip system for gripping soft materials, said gripping system comprising:
   (a) first and second adjustably spaced apart opposed gripping devices, each of said first and second gripping devices having an outer gripping surface;
   (b) a thermo-electric cooler adapted for cooling the outer gripping surface of each of said first and second gripping devices, wherein the thermo-electric cooler is isolated electrically from the outer gripping surface of each of said first and second gripping devices; and
   (c) mechanically adjustable actuating devices coupled to said first and second gripping devices, wherein said actuating devices actuate said first and second gripping devices to change a separation distance between said first and second gripping devices to capture an object therebetween and thereafter to adjust the gripping force on a captured object to secure said captured object in place.

2. A thermo-electric system as in claim 1 wherein said mechanically adjustable actuating devices include rotatable screw devices.

3. A thermo-electric system as in claim 1 wherein said mechanically adjustable actuating devices include a hand-held scissor arrangement.

4. A thermo-electric system as in claim 1 wherein said mechanically adjustable actuating devices include tension members of a forceps.

5. A thermo-electric gripping system as recited in claim 1, further including a controller electrically coupled to said thermo-electric cooler to control a temperature at the outer gripping surface of each of said first and second gripping devices.

6. A thermo-electric gripping system as recited in claim 5 wherein the controller controls a rate of cooling the outer gripping surface of each of said first and second gripping devices.

7. A thermo-electric gripping system as recited in claim 2, further including a controller electrically coupled to said thermo-electric cooler to control a temperature at the outer gripping surface of each or said first and second gripping devices.

8. A thermo-electric gripping system as recited in claim 7 wherein the controller controls a rate of cooling the outer gripping surface of each of said first and second gripping devices.

9. A thermo-electric gripping system as recited in claim 3, further including a controller electrically coupled to said thermo-electric cooler to control a temperature at the outer gripping surface of each of said first and second gripping devices.

10. A thermo-electric gripping system as recited in claim 9 wherein the controller controls a rate of cooling the outer gripping surface of each of said first and second gripping devices.

11. A thermo-electric gripping system as recited in claim 4, further including a controller electrically coupled to said thermo-electric cooler to control a temperature at the outer gripping surface of each of said first and second gripping devices.

12. A thermo-electric gripping system as recited in claim 11 wherein the controller controls a rate of cooling the outer gripping surface of each of said first and second gripping devices.

13. A thermo-electric gripping system as recited in claim 1 wherein the outer gripping surface of each of said first and second gripping devices includes a removable jaw plate.

14. A thermo-electric gripping system as recited in claim 13 wherein the jaw plate includes an outer contoured surface suitable for gripping various sized soft materials.

15. A thermo-electric gripping system as recited in claim 2 wherein the outer gripping surface of each of said first and second gripping devices includes a removable jaw plate.

16. A thermo-electric gripping system as recited in claim 15 wherein the jaw plate includes an outer contoured surface suitable for gripping various sized soft materials.

17. A thermo-electric gripping system as recited in claim 3 wherein the outer gripping surface of each of said first and second gripping devices includes a removable jaw plate.

18. A thermo-electric gripping system as recited in claim 17 wherein the jaw plate includes an outer contoured surface suitable for gripping various sized soft materials.

19. A thermo-electric gripping system as recited in claim 4 wherein the outer gripping surface of each of said first and second gripping devices includes a removable jaw plate.

20. A thermo-electric gripping system as recited in claim 19 wherein the jaw plate includes an outer contoured surface suitable for gripping various sized soft materials.

21. A thermo-electric gripping system as recited in claim 1 further including a cooling conduit coupled to said first and said second gripping devices for providing a passage for coolant to said thermo-electric coolers.

22. A thermo-electric gripping system as recited in claim 1 wherein said gripping system freezes soft tissue material that contacts said outer gripping surface of each of said first and second gripping devices.

23. A thermo-electric gripping system as recited in claim 3 wherein said gripping system forms a gripping end of a surgical instrument.

24. A thermo-electric gripping system as recited in claim 5 wherein said controller includes a temperature sensing device.

\* \* \* \* \*